(12) United States Patent
Reed et al.

(10) Patent No.: US 9,533,240 B2
(45) Date of Patent: Jan. 3, 2017

(54) SYSTEM AND METHOD FOR EMULSION BREAKING

(71) Applicant: LIFE TECHNOLOGIES CORPORATION, Carlsbad, CA (US)

(72) Inventors: Brian Reed, Woodbridge, CT (US); James A. Ball, Ledyard, CT (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/536,429

(22) Filed: Nov. 7, 2014

(65) Prior Publication Data

US 2015/0133649 A1 May 14, 2015

Related U.S. Application Data

(60) Provisional application No. 61/942,167, filed on Feb. 20, 2014, provisional application No. 61/902,897, filed on Nov. 12, 2013.

(51) Int. Cl.

| C07H 21/00 | (2006.01) |
|---|---|
| C07H 1/06 | (2006.01) |
| C12Q 1/68 | (2006.01) |
| B01D 17/04 | (2006.01) |

(52) U.S. Cl.
CPC ............ *B01D 17/04* (2013.01); *C07H 1/06* (2013.01); *C07H 21/00* (2013.01); *C12Q 1/6806* (2013.01)

(58) Field of Classification Search
CPC ......... C07H 21/00; C07H 1/06; C12Q 1/6806; B01D 17/04
USPC .............................................. 536/25.4, 124
See application file for complete search history.

(56) References Cited

U.S. PATENT DOCUMENTS

| 3,258,453 | A | * | 6/1966 | Chi | .............. C08F 6/24 526/346 |
|---|---|---|---|---|---|
| 5,055,408 | A | | 10/1991 | Higo et al. | |
| 5,647,994 | A | | 7/1997 | Tuunanen et al. | |
| 6,033,574 | A | | 3/2000 | Siddiqi et al. | |
| 6,413,780 | B1 | | 7/2002 | Bach et al. | |
| 7,842,457 | B2 | | 11/2010 | Berka et al. | |
| 8,025,788 | B2 | * | 9/2011 | Cardosi | ............ C12Q 1/001 205/777.5 |
| 8,562,920 | B2 | | 10/2013 | Tajima | |
| 2005/0013741 | A1 | | 1/2005 | a'Brassard | |
| 2005/0047963 | A1 | | 3/2005 | Safar et al. | |
| 2006/0211080 | A1 | | 9/2006 | Frost et al. | |
| 2007/0214900 | A1 | | 9/2007 | Porat et al. | |
| 2008/0003571 | A1 | | 1/2008 | McKernan et al. | |
| 2010/0137165 | A1 | | 6/2010 | Tajima | |
| 2011/0087016 | A1 | | 4/2011 | Suo | |
| 2013/0131053 | A1 | * | 5/2013 | Nanchen | ............ A01N 43/80 514/227.8 |
| 2013/0164789 | A1 | | 6/2013 | Schultz et al. | |

FOREIGN PATENT DOCUMENTS

| EP | 2333560 | 6/2011 |
|---|---|---|
| WO | 2007/086935 | 8/2007 |
| WO | 2007/149432 | 12/2007 |
| WO | 2008/052138 | 5/2008 |
| WO | 2012036679 | 3/2012 |
| WO | 2012/138926 | 10/2012 |
| WO | 2013/016459 | 1/2013 |

OTHER PUBLICATIONS

Chunsun, Zhang et al., "Single-Molecule DNA Amplification and Analysis Using Microfluidics", *Chem. Rev.* vol. 110, 2010, pp. 4910-4947.
International Search Report and Written Opinion of the International Searching Authority for International Application No. PCT/US2014/064675 mailed Mar. 5, 2015, 13 pages.
Invitation to Pay Additional Fees—Partial Search Report for International Application No. PCT/US2012/045860 mailed Sep. 24, 2012.
International Search Report and Written Opinion for International Application No. PCT/US2012/045860 mailed Nov. 15, 2012.

* cited by examiner

*Primary Examiner* — Sudhakar Katakam
*Assistant Examiner* — Everett White (57) ABSTRACT

A method of recovering a bead support from an emulsion includes supplying an aqueous surfactant solution into a centrifuge tube; supplying a hydrophobic liquid over the surfactant solution in the centrifuge tube, wherein a ratio of the volume of the aqueous surfactant solution to the volume of the hydrophobic liquid is not greater than 0.5; and applying an emulsion over the hydrophobic liquid while centrifuging, the emulsion comprising a dispersed aqueous phase including the bead support, the emulsion breaking and material of the dispersed phase preferentially partitioning to the surfactant solution.

20 Claims, 8 Drawing Sheets

SYSTEM AND METHOD FOR EMULSION BREAKING

CROSS-REFERENCE TO RELATED APPLICATION(S)

This application claims benefit of U.S. Provisional Application No. 61/902,897, filed Nov. 12, 2013, which is incorporated herein by reference in its entirety.

This application claims benefit of U.S. Provisional Application No. 61/942,167, filed Feb. 20, 2014, which is incorporated herein by reference in its entirety.

FIELD OF THE DISCLOSURE

This disclosure, in general, relates to systems and methods for breaking emulsions.

BACKGROUND

Emulsions are utilized in a range of industries, including the food, biological sciences, and chemical industries. In particular, the chemical and biological sciences industries utilize emulsions to isolate volumes of reactants. For example, the chemical industry utilizes emulsions for emulsion polymerization in which small volumes of monomers in solution are isolated as a dispersed phase and subsequently polymerized. In the biological sciences, particularly the genetic sciences, emulsions have been used to isolate genetic material into dispersed volumes, limiting cross-contamination between the dispersed volumes. In a particular example, emulsions are utilized to isolate volumes that include a bead support and a polynucleotide to be amplified. For example, a polynucleotide isolated in a small volume with a bead support, primers, a variety of nucleotides, enzymes, and other cofactors can be subjected to amplification conditions to facilitate the formation of nucleic acid beads incorporating the amplified polynucleotide or complements thereof.

While the principles of amplification are understood, the process or automation of this process has proven difficult. In particular, automation of the formation of the emulsion is challenging. Moreover, automating the recovery of the bead supports from an emulsion following amplification has proven challenging. Often, a significant portion of the bead supports to which products of the amplified polynucleotide are attached are lost during the separation of the bead supports from the emulsion. As such, the yield of bead supports conjugated to polynucleotides is diminished. Such a loss of yield can adversely affect genetic testing methods.

SUMMARY

In an example, a method of recovering a bead support from an emulsion includes supplying an aqueous surfactant solution into a centrifuge tube; supplying a hydrophobic liquid over the surfactant solution in the centrifuge tube, wherein a ratio of the volume of the aqueous surfactant solution to the volume of the hydrophobic liquid is not greater than 0.5; and applying an emulsion over the hydrophobic liquid while centrifuging, the emulsion comprising a dispersed aqueous phase including the bead support, the emulsion breaking and material of the dispersed phase preferentially partitioning to the surfactant solution.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

In an exemplary embodiment, a method of recovering a bead support from an emulsion includes applying an aqueous surfactant solution into a centrifuge tube. A hydrophobic liquid is applied over the surfactant solution in the centrifuge tube. In an example, the ratio of the volume of the aqueous surfactant solution to the volume of the hydrophobic liquid is not greater than 1.0, such is not greater than 0.5. Alternatively, the ratio of the initial volume of the aqueous surfactant solution to the total volume of the centrifuge tube is not greater than 0.5, such as not greater than 0.2 or not greater than 0.1. The centrifuge tube can be located within a centrifuge rotor. While rotating the centrifuge rotor including the centrifuge tube, an emulsion can be applied over the hydrophobic liquid. The emulsion includes a dispersed aqueous phase including the bead support. As the emulsion breaks, material of the dispersed phase, including the bead support, can preferentially partition into the surfactant solution. As such, the bead support is driven into the aqueous surfactant solution toward the bottom of the centrifuge tube in response to centrifugal force. The aqueous surfactant solution can include a non-ionic surfactant or can include an anionic surfactant. In an example, the non-ionic surfactant includes a polyethylene glycol ether, an alkyl pyrrolidine, an alkyl imidazolidinone, an alkyl morpholine, an alkyl imidazole, an alkyl imidazoline, or a combination thereof. In another example, the non-ionic surfactant includes a non-ionic fluorosurfactant. In a further example, the anionic surfactant includes a sulfate or sulfonate surfactant. The recovered bead supports, when recovered as part of a genetic testing system, can be applied to a sequencing device and sequencing can be performed.

Figure 1:
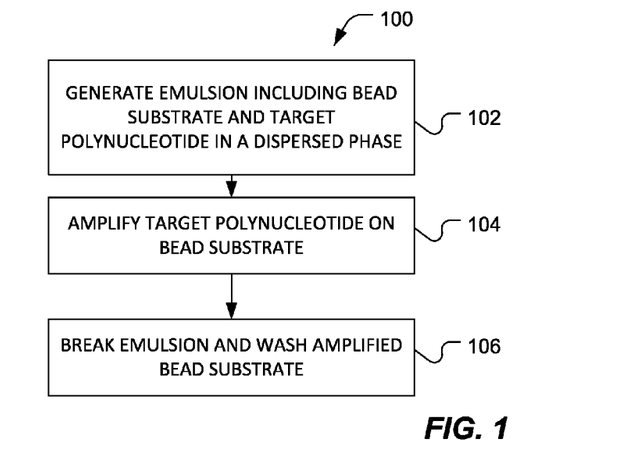
FIG. 1 includes a block flow diagram illustrating an exemplary method for recovering an amplified bead substrate.

For example, FIG. 1 includes an illustration of an exemplary method 100 in which an emulsion is generated, as illustrated at 102. The emulsion includes a bead support and a target polynucleotide in a dispersed phase. For example, reactants and cofactors along with a bead support and a target polynucleotide can be isolated in small volumes of aqueous solution as the dispersed phase.

The bead support can be formed of a polymer. An exemplary polymer includes acrylamide, vinyl acetate, hydroxyalkylmethacrylate, a polyethylene glycol, derivations thereof or any combination thereof. In an example, the bead support includes functional sites to which other species, such as an oligonucleotide primer, click chemistry, or a binding agent, such as biotin or streptavidin, can be attached. In particular, the polymer of the bead support can be formed with an Acrydite™ comonomer having an acrylate modified with an oligonucleotide. In another example, the polymer bead support can include an amine or hydroxyl group that can be reactive with additional agents, such as halides, amines, azide, cyanuric acid, di-isocyanate, bis-NHS esters, or any combination thereof, attached, for example, to a protein or oligonucleotide.

In the emulsion, an aqueous phase is distributed in a hydrophobic phase. In an example, the hydrophobic phase can include fluorinated liquids, minerals oils, silicone oils, or any combination thereof. Optionally, the hydrophobic phase can include a surfactant, such as a non-ionic surfactant, such as a non-ionic surfactant described below.

The emulsion can be subjected to amplification conditions and as a result, the target polynucleotide can be amplified and the products of such an amplification can attached to the bead support, as illustrated at 104, forming a template bead support. For example, the target polynucleotide can be amplified using a polymerase chain reaction (PCR). In another example, the target polynucleotide can be amplified using recombinase polymerase amplification (RPA), such as isothermal RPA.

Following amplification, the emulsion can be broken, as illustrated at 106, and the templated bead support washed. For example, the emulsion can be applied continuously, such as in a stream, to a centrifuge tube disposed on a rotating rotor of a centrifuge. The centrifuge tube can include an aqueous surfactant solution and optionally, the hydrophobic liquid disposed over the aqueous surfactant solution. When the emulsion is applied to the hydrophobic liquid, the dispersed phase is driven to the interface between the hydrophobic liquid and the surfactant solution. At the interface, the emulsion can break, driving the bead support associated with the dispersed phase into the surfactant solution and toward the bottom of the centrifuge tube.

In a particular example, hydrophobic liquid includes fluorinated liquids, minerals oils, silicone oils, or any combination thereof. The hydrophobic liquid can further include a surfactant, such as a non-ionic surfactant. Exemplary non-ionic surfactants are described below. In particular, the hydrophobic liquid is miscible with the continuous phase of the emulsion. For example, the hydrophobic liquid can have the same or similar composition to that of the continuous phase of the emulsion.

In particular, the emulsion is broken at an interface between the surfactant solution and the hydrophobic liquid. As such, it has been found that the relative volumes and in particular, the associated distance that the dispersed phase of the emulsion travels as it is applied over the hydrophobic liquid influences the yield of bead supports from the emulsion.

Figure 2:
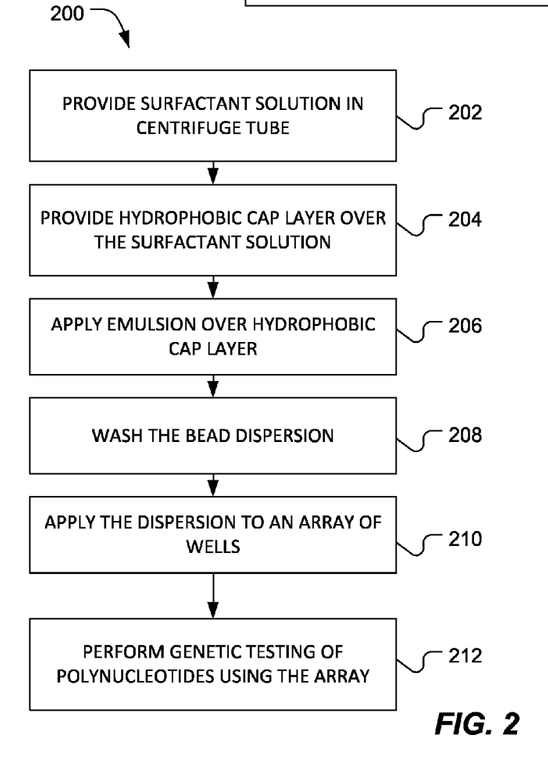
FIG. 2 includes a block flow diagram illustrating an exemplary method for breaking an emulsion.

For example, a method 200 for breaking emulsion is illustrated in FIG. 2. The method 200 includes providing an aqueous surfactant solution in a centrifuge tube, as illustrated at 202. In a particular example, the initial volume of aqueous solution is in a range of 50 µL to 1 mL, such as a range of 50 µL to 500 µL, a range of 50 µL to 250 µL, or even a range of 50 µL to 150 µL.

In an example, the surfactant solution can include one or more surfactants having a total concentration in the range of 0.01% to 20% by weight. For example, surfactant can be included in a total amount in a range of 0.1% to 15.0%, such as a range of 0.5% to 10.0%, a range of 0.5% to 5.0% or even a range of 0.5% to 3% by weight. In another example, surfactant can be included in a total amount in a range of 5.0% to 20.0%, such as a range of 10.0% to 20.0%, or a range of 12.0% to 18.0%.

The surfactant can be an ionic surfactant, an amphoteric surfactant, or a non-ionic surfactant. The ionic surfactant can be an anionic surfactant. An exemplary anionic surfactant includes a sulfate surfactant, a sulfonate surfactant, a phosphate surfactant, a carboxylate surfactant, or any combination thereof. An exemplary sulfate surfactant includes alkyl sulfates, such as ammonium lauryl sulfate, sodium lauryl sulfate (sodium dodecyl sulfate, (SDS)), or a combination thereof; an alkyl ether sulfate, such as sodium laureth sulfate, sodium myreth sulfate, or any combination thereof; or any combination thereof. An exemplary sulfonate surfactant includes an alkyl sulfonate, such as sodium dodecyl sulfonate; docusates such as dioctyl sodium sulfosuccinate; alkyl benzyl sulfonate (e.g., dodecyl benzene sulfonic acid or salts thereof); or any combination thereof. An exemplary phosphate surfactant includes alkyl aryl ether phosphate, alkyl ether phosphate, or any combination thereof. An exemplary carboxylic acid surfactant includes alkyl carboxylates, such as fatty acid salts or sodium stearate; sodium lauroyl sarcosinate; a bile acid salt, such as sodium deoxycholate; or any combination thereof.

In another example, the ionic surfactant can be a cationic surfactant. An exemplary cationic surfactant includes primary, secondary or tertiary amines, quaternary ammonium surfactants, or any combination thereof. An exemplary quaternary ammonium surfactant includes alkyltrimethylammonium salts, such as cetyl trimethylammonium bromide (CTAB) or cetyl trimethylammonium chloride (CTAC); cetylpyridinium chloride (CPC); polyethoxylated tallow amine (POEA); benzalkonium chloride (BAC); benzethonium chloride (BZT); 5-bromo-5-nitro-1,3-dioxane; dimethyldioctadecylammonium chloride; dioctadecyldimethylammonium bromide (DODAB); or any combination thereof.

An exemplary amphoteric surfactant includes a primary, secondary, or tertiary amine or a quaternary ammonium cation with a sulfonate, carboxylate, or phosphate anion. An exemplary sulfonate amphoteric surfactant includes (3-[(3-cholamidopropyl)dimethylammonio]-1-propanesulfonate); a sultaine such as cocamidopropyl hydroxysultaine; or any combination thereof. An exemplary carboxylic acid amphoteric surfactant includes amino acids, imino acids, betaines such as cocamidopropyl betaine, or any combination thereof. An exemplary phosphate amphoteric surfactant includes lecithin.

In another example, the surfactant can be a non-ionic surfactant such as a polyethylene glycol-based surfactant, an alkyl pyrrolidine surfactant, an alkyl imidazolidinone surfactant, an alkyl morpholine surfactant, an alkyl imidazole surfactant, an alkyl imidazoline surfactant, or a combination thereof. In a particular example, the polyethylene-glycol-based surfactant includes a polyethylene-glycol ether, such as an alkylphenol polyethoxylate. In another example, the non-ionic surfactant includes a non-ionic fluorosurfactant, such as an ethoxylated fluorocarbon. In a further example, the surfactant solution can include octyl pyrrolidine.

In particular, the surfactant solution can include combinations of such surfactants. For example, the surfactant solution can include a combination of a non-ionic surfactant with an anionic surfactant. In a particular example, the surfactant solution can include a non-ionic surfactant, such as a polyethylene glycol ether, an alkyl pyrrolidine, or a non-ionic fluorosurfactant, and an anionic surfactant, such as a sulfate surfactant, for example SDS. In particular, the surfactant solution can include an ionic surfactant, such as an anionic surfactant, in an amount in a range of 0.1% to 20.0%, such as a range of 1.0% to 15.0%, or a range of 5.0% to 15.0%, or a range of 8.0% to 12.0%. In addition, the surfactant solution can include a non-ionic surfactant, such as alkyl pyrrolidine (e.g., octyl pyrrolidine), in a range of 0.01% to 10.0%, such as a range of 0.05% to 8.0%, or a range of 1.0% to 6.0%. In another example, the surfactant solution can include a non-ionic surfactant in a range of 0.05% to 3.0%.

Optionally, a hydrophobic liquid can be applied as a capping layer over the surfactant solution, as illustrated at 204 in FIG. 2. Optionally, the hydrophobic liquid can be applied to the surfactant solution while the centrifuge is rotating. For example, the hydrophobic liquid can include an oil, such as a natural oil or a synthetic oil. Exemplary oils include fluorinated liquids, minerals oils, silicone oils, or any combination thereof, or any other suitable oil. In an example, the hydrophobic liquid can include a surfactant, such as a non-ionic surfactant described above. In another example, the hydrophobic liquid is miscible with the continuous phase of the emulsion. In particular, the hydrophobic liquid can have the same or similar composition to the continuous phase of the emulsion.

In an example, the initial volume of the hydrophobic liquid is in a range of 100 μL to 10 mL, such as a range of 200 μL to 5 mL, a range of 300 μL to 2.7 mL, or even a range of 500 μL to 2 mL. The initial ratio of the volume of the surfactant solution relative to the volume of the hydrophobic liquid applied over the surfactant solution is not greater than 1.0. For example, the ratio can be not greater than 0.5, such as not greater than 0.25, not greater than 0.1, or even not greater than 0.05. In general, the ratio is at least 0.01. As a result of the volume difference, the relative heights of the solutions within the centrifuge tube have a ratio of approximately that of the ratio of the volume. Alternatively, the initial volume of the hydrophobic liquid can be provided during centrifugation or as part of dispensing the emulsion.

In an example, the centrifuge tube can have a total volume in a range of 0.7 mL to 5 mL, such as a range of 0.8 mL to 3 mL, a range of 1.0 mL to 2.5 mL, or even a range of 1.5 mL to 2.5 mL. The initial ratio of the volume of the surfactant solution relative to the volume of the centrifuge tube is not greater than 1.0. For example, the ratio can be not greater than 0.5, such as not greater than 0.25, not greater than 0.1, or even not greater than 0.05. In general, the ratio is at least 0.01.

Figure 3:
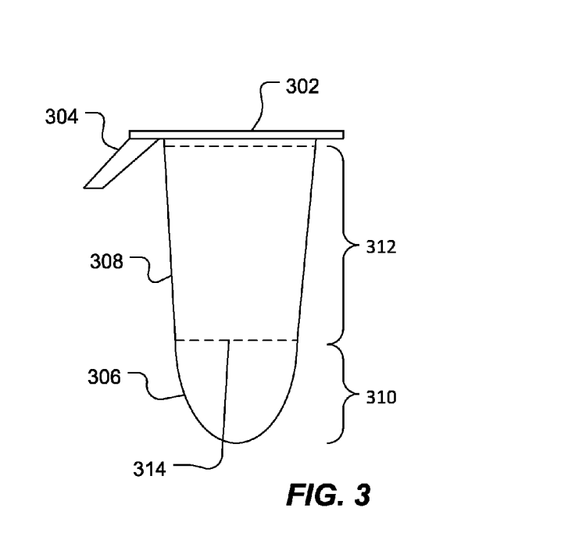
FIG. 3 includes an illustration of an exemplary centrifuge tube.

For example, as illustrated by the centrifuge tube 302 of FIG. 3, the surfactant solution 306 underlies the hydrophobic liquid forming layer 308. The surfactant solution 306 has a height 310 and the hydrophobic liquid forms a layer 308 having a second height 312. As illustrated, the height 312 of the hydrophobic liquid can be the same or greater than the height 310 of the surfactant solution. The centrifuge tube 302 can also include a channel 304 through which additional material such as portions of the hydrophobic liquid or the continuous phase of the emulsion can be driven from the centrifuge tube 302 as the emulsion is applied to the centrifuge tube and the aqueous dispersed phase is driven towards the interface 314 between the hydrophobic liquid 308 and the surfactant solution 306.

For example, a ratio of the initial height of the surfactant solution to the initial height of the hydrophobic liquid is not greater than 1.0, such as not greater than 0.5, not greater than 0.25, not greater than 0.1, or even not greater than 0.05. In particular, the ratio of heights can be at least 0.01. Initially, the cumulative volume of the aqueous surfactant solution and the hydrophobic liquid occupy a significant volume of the centrifuge tube. For example, the cumulative volume can occupy at least 80% of the tube volume, such as at least 90% of the tube volume, at least 95% of the tube volume, or even 100% of the tube volume.

As illustrated at 206 in FIG. 2, the emulsion is applied to the hydrophobic capping layer. In particular, the emulsion can be applied while the centrifuge is rotating. When applied, the dispersed phase of the emulsion travels through the hydrophobic layer and concentrates. The dispersed phase is driven into the surfactant solution. The bead supports within the dispersed phase are released into the surfactant solution and are driven to the bottom of the centrifuge tube. As the emulsion is applied, the relative volumes of the aqueous phase and the hydrophobic phase can change.

After the emulsion is broken, the bead supports are dispersed within the solution. The aqueous solution can be washed, as illustrated at 208 in FIG. 2. For example, additional surfactant solution can be applied over the bead supports to further remove oil and other contaminants. The wash solution can further include a sodium salt.

In an example, a significant portion of the bead supports are recovered following emulsion breaking. For example, at least 70% of the bead supports in the emulsion can be recovered in the surfactant solution. In particular, at least 80% of the bead supports can be recovered, such as at least 85%, at least 90%, or even at least 95%, but not greater than 100% of the bead supports can be recovered.

In a particular example in which the bead supports act as a support for an amplification product for use in a genetic testing system, a dispersion including the bead support conjugated to amplification product can be applied to an array of wells, as illustrated in FIG. 2 at 210. The array of wells can form part of a device for use in a genetic sequencing system. As such, genetic testing can be performed on the polynucleotides conjugated to the bead supports, as illustrated at 212.

Such a method is particularly useful in an automated system for breaking emulsion, in particular, those incorporated in an automated system for recovering bead supports conjugated to an amplification product. In an example, FIG. 4, FIG. 7, FIG. 8, FIG. 9, FIG. 10, and FIG. 11 illustrate a centrifuge subsystem 700. A lid can be in the open configuration such that the interior of the centrifuge 700 can be seen as well as the top housing rim on which the lid rests while in a closed configuration. A rotor 832 having a rotor housing 836 is visible through top housing aperture 840 defined by top housing room 828. Centrifuge 700 provides a housing basin that is visible and defined by the top housing room 828. Housing basin 844 provides basin sidewalls 848 as well as a receiving platform 852. Receiving platform 852 comprises motor mounting apertures 856 as well as a central rotor axle aperture 860.

Figure 4:
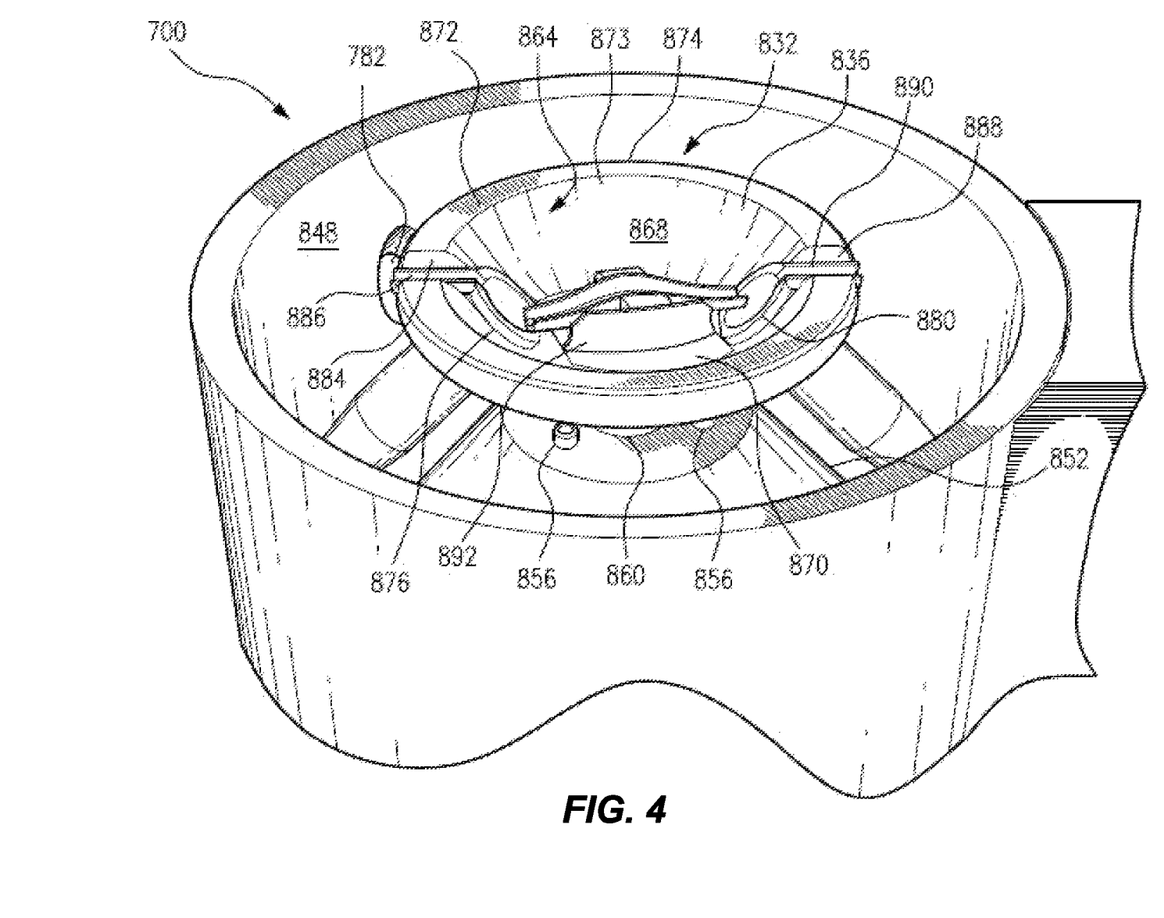
FIG. 4 includes an illustration of an exemplary centrifuge rotor.

The rotor 832 and its rotor basin 864 comprise rotor basin sidewalls 868 and rotor basin floor 870 and a rotor top rim 872 around the periphery and upper end of rotor basin sidewalls 868. Rotor basin sidewalls 868 provide at least one collection tube receptacle. The rotor basin sidewalls 868 provide first tube receptacle 876 and second tube receptacle 880. Any number of tube receptacles can be provided in rotor basin sidewall depending in part on the size of the tubes to be inserted and the overall size and surface area of the rotor basin sidewall 868. Rotor top rim 872 has an inner perimeter 873 and outer perimeter 874. Alongside the respective tube receptacles and provided in rotor top rim 872 are collection tube exit channels receptacles. As illustrated in FIG. 4, first tube exit channel receptacle 884 and second tube exit channel receptacle 888 are provided respectively with first and second receptacle grooves 886, 890. At the center of the rotor basin 864 is a fluid distribution device or slinger receptacle 892 comprising slinger receptacle sidewalls 894.

A fluid collection tube is provided comprising a main tube body and a tube extension. The main tube body can comprise a main body sidewall surrounding a tube interior comprising a tube opening at a first end, and a second end distal to the first end providing a sealed base. The tube extension can comprise a tube extension sidewall defining a fluid exit channel in fluid communication with the tube interior through a tube channel inlet proximal to the tube opening and extending to a tube channel outlet distal to the tube opening. The fluid collection tube can further comprise a tube lip disposed about the perimeter of the tube opening and allowing fluid communication of the tube exit channel with the tube interior. An optional tube buttress disposed between the tube extension sidewall and the main tube sidewall provides further support and rigidity. The tube extension sidewall and the main tube sidewall can be positioned at any angle relative to one another, from about 15° to about 90°, from about 1.0° to about 80°, from about 5.0° to about 75°, from about 10° to about 65°, from about 20° to about 60°, from about 25° to about 50°, from about 30° to about 45°, from about 30° to about 60°, from about 40° to about 50°, or greater than about 90° relative to each other.

The fluid collection tube can be provided in any suitable shape including the main tube body and the tube extension. For example, the main tube body can comprise a generally cylindrical portion proximal the first end, a conically tapered portion proximal the second end, and a rounded second end. For example, the tube exit channel and tube extension sidewall can have a U-shaped cross-section along a longitudinal axis. The average cross-sectional area of the exit tube channel can be less than, equal to, or greater than the average cross-sectional area of the tube interior. The average cross-sectional area of the exit tube channel can be less than about 95%, less than about 90%, less than about 75%, less than about 60%, less than about 50%, less than about 40%, less than about 25%, less than about 20%, less than about 15%, less than about 10%, less than about 5%, or less than about 1%, but at least 0.001% of the average cross-sectional area of the tube interior.

The fluid collection tube can optionally comprise a cap or lid. The lid can be completely separable from the tube housing or can be permanently joined to the housing, for example, through a flexible hinge. The cap can be configured to close off the main tube interior, the fluid exit channel, or both.

The fluid collection tube can be constructed from any suitable material. Suitable materials include metals, plastics, glass, ceramics, or any combination thereof. Examples of suitable plastics include polypropylene, polycarbonate, and polyvinyl chloride. The fluid collection tube can be constructed to contain any desired volume. The fluid collection tube can have a volume of less than about 1 μL, from about 1 μL to about 1 L, from about 10 μL to about 1 dL, from about 100 μL to about 1 cL, from about 500 μL to about 50 mL, from about 1 mL to about 25 mL, from about 2.5 mL to about 15 mL, or from about 5 mL to about 10 mL.

Figure 5:
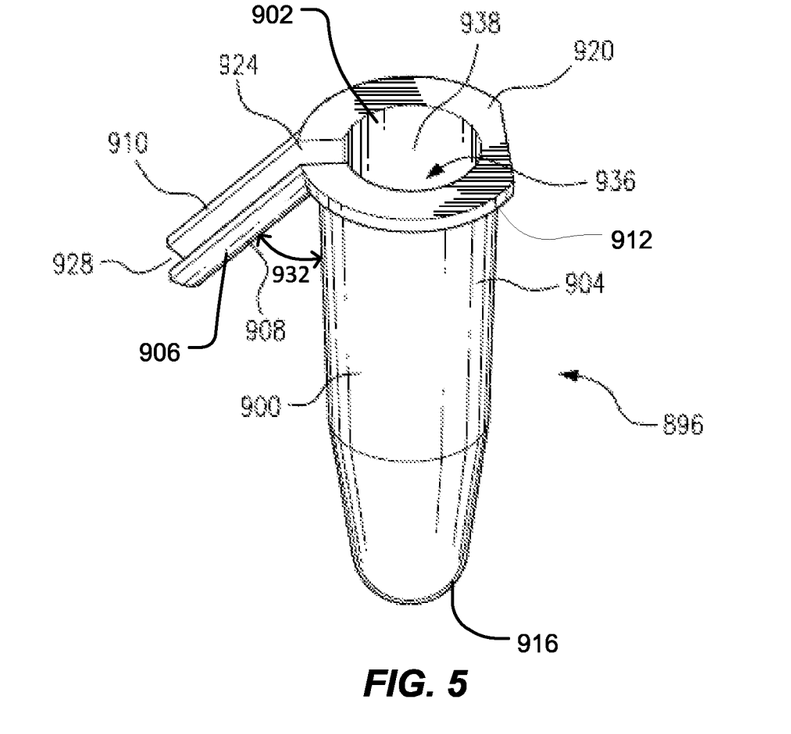
FIG. 5 includes an illustration of an exemplary centrifuge tube.

FIG. 5 illustrates a centrifuge tube or collection tube 896. The collection tube 896 comprises a tube housing 900 including a main tube body 904, comprising a tube interior 902, and a tube extension 906 comprising a fluid exit channel 908. The length of the collection tube is defined by a first tube end 912 and a second tube end 916. At first tube end 912, is a tube lip 920 that can be engaged by rotor sidewall apertures tube receptacles 876, 880. Fluid exit channel 908 has a length defined by a tube channel inlet 924 and a tube channel outlet 928.

In particular, an angle 932 is shown defined by the spacing of the side walls 910 of tube extension 906 from main tube body 904. An optional tube buttress can be formed between the main tube body and the tube extension. Tube inlet 920 defines and surrounds a tube opening (aperture) 936 having a tube opening center 938. At the middle of tube opening 936 is tube opening center 938.

Figure 6:
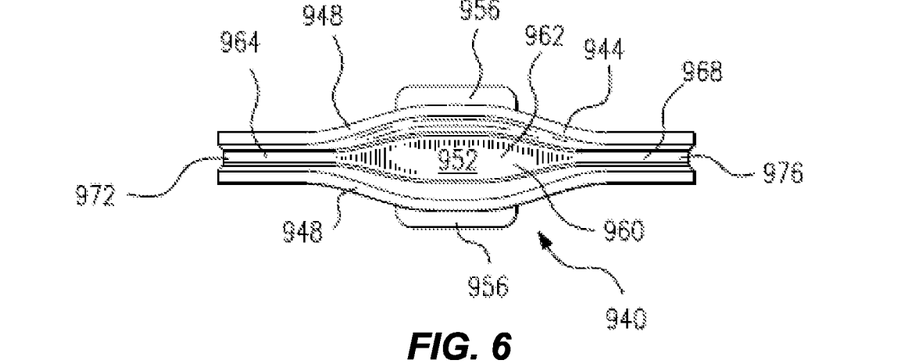
FIG. 6 includes an illustration of an exemplary slinger or distributor.

A fluid distribution device 940, also referred to herein as a "slinger," is illustrated in FIG. 6. The slinger can comprise sidewalls defining a central channel comprising a first end, a central zone, and a second end along a longitudinal axis. Sidewall lateral extensions also referred to as "wings" herein, can be provided, extending away from the sidewalls on either side of the central channel. The wings are useful in mating with and ensuring a secure connection with a fluid distribution device receptacle of a centrifuge rotor. The slinger can have any number of spouts that can be correlated with the number of fluid collection tubes to be used in conjunction with the slinger. For example, when two fluid collection tubes are employed, the slinger can include a first spout extending from the central zone to the first end and terminating at a first spout outlet, the sidewalls tapering along the central zone toward the first spout; and a second spout extending from the central zone to the second end and terminating at a second spout outlet, the sidewalls tapering along the central zone toward the second spout.

The slinger can be configured to mate with a fluid distribution device receptacle of a centrifuge rotor using any suitable configuration. For example, wings, as described herein, can be employed. Rather than use an insertable/detachable slinger, a slinger can be employed that is permanently or integrally associated with the rotor housing.

The slinger can be fabricated from any suitable material or materials such as those described herein for the collection tube. The slinger can comprise one or more of the materials described herein for the fluid collection tubes. The slinger can have any desired volume. The slinger can have a volume or less than about 1 μL, from about 1 μL to about 1 L, from about 10 μL to about 1 dL, from about 100 μL to about 1 cL, from about 500 μL to about 50 mL, from about 1 mL to about 25 mL, from about 2.5 mL to about 15 mL, or from about 5 mL to about 10 mL.

FIG. 6 is a plan view of a liquid distribution device or slinger 940. Slinger 940 comprises a slinger housing 944, which is shaped to provide slinger sidewalls 948, a slinger base 952, and slinger wings 956. A slinger central channel 960 is defined by the slinger base 952 and slinger sidewalls 948 running the length of the slinger. At the center of the slinger is a central zone 962. While the slinger 940 is shown having a single central channel 960, additional central channels can be provided in other embodiments. First slinger spout 964 and second slinger spout 968 comprise opposite sides and ends of the slinger central channel 960. At either end of slinger central channel 960 as well as the ends of respective first slinger spouts 964, 968 are first slinger spout outlet 972 and second slinger spout outlet 976.

A centrifuge rotor, which is particularly suitable for separating water-in-oil emulsions and removing the oil phase of such an emulsion. The centrifuge rotor can comprise a rotor housing having a bisecting rotor axis perpendicular to a central rotor axis, a rotor basin formed by the rotor housing, a rotor basin floor, and a rotor basin sidewall lining the rotor housing basin and extending up toward a rotor top rim having an inner perimeter and an outer perimeter. The rotor can further comprise at least one collection tube receptacle comprising an opening formed in the basin sidewall, and at least one tube extension receptacle having a grove formed in the rotor top rim and extending from the inner perimeter to the outer perimeter. The sidewalls can comprise a substantially flat inset region about the collection tube receptacle and adjacent the tube receptacle opening.

The centrifuge rotor can be provided with any number of collection tube receptacles and corresponding tube extensions. Generally, an even number of receptacles are provided on opposite sides of the rotor basin. For example, first and second tube receptacles positioned opposite each other along the bisecting rotor axis; and first and second tube extension grooves opposite each other along the bisecting rotor axis. An odd number of receptacles can be utilized, and in such embodiments the rotor can be balanced to account for the weight of any unpaired receptacles. Balancing can also be provided for embodiments where an even number of receptacles are provided but when not all receptacles are fitted with collection tubes or collection tubes of unequal volume or weight. The rotor can also comprise at least one liquid distribution device (slinger) receptacle extending from the rotor basin floor and having a distribution device receptacle longitudinal axis.

The collection tube receptacle opening and the tube extension groove are generally positioned at an angle relative to each other corresponding to the angle of the tube extension sidewall relative to the main tube body. For example, the collect tube receptacle and the tube extension groove can be from about 15° to about 90°, from about 1.0° to about 80°, from about 5.0° to about 75°, from about 10° to about 65°, from about 20° to about 60°, from about 25° to about 50°, from about 30° to about 45°, from about 30° to about 60°, from about 40° to about 50°, or greater than about 90° relative to each other. The shape of the rotor sidewall can be configured to accommodate a collection tube buttress. The fluid distribution device receptacle can include a means for receiving or reversibly locking in place the slinger. For example, the slinger receptacle can contain opposing sidewalls on either side of the distribution device receptacle longitudinal axis that can cooperate with wings on the slinger.

The slinger receptacle can be provided in any suitable configuration within the centrifuge rotor. The bisecting rotor axis can be parallel or non-parallel to the distribution device receptacle longitudinal axis. The axes can be positioned from about 0.01° to about 25°, from about 0.05° to about 20°, from about 0.15° to about 15.0°, from about 0.25° to about 10.0°, from about 0.5° to about 5.0°, from about 1.0° to about 2.5°, less than about 0.01°, or greater than about 25° relative to each other.

Figure 7:
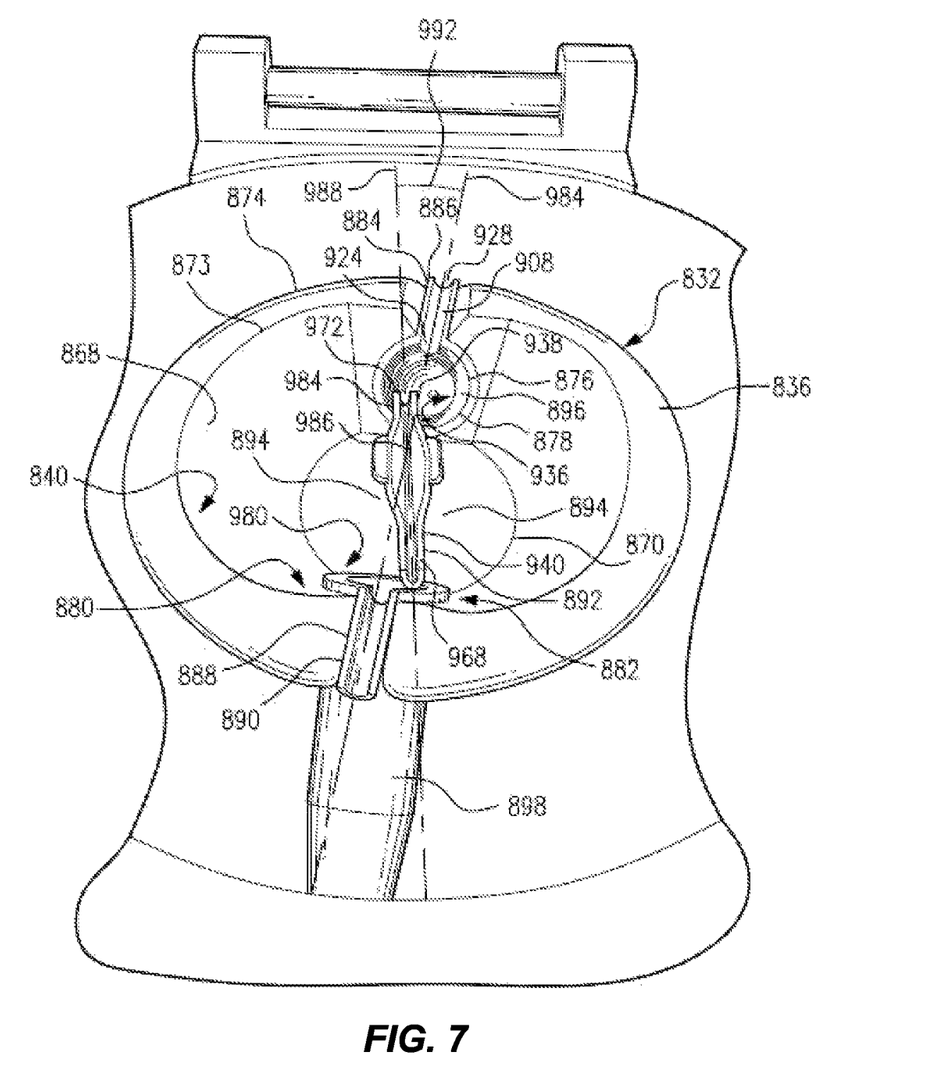
FIG. 7, FIG. 8, FIG. 9, FIG. 10, and FIG. 11 include illustrations of an exemplary centrifuge device.

FIG. 7 is a top perspective view of rotor 832 as positioned in housing basin 844. First collection tube 896 and second collection tube 898 are disposed in respective first and second tube receptacles 876 and 880. Slinger 940 is positioned in slinger receptacle 892. Collection tubes 896 and 898 each have respective tube openings 936 and 980, which in turn have respective tube opening centers 938 and 882. Cutting the rotor approximately in half is a bisecting rotor axis 984, which can be perpendicular to central rotor axis 986, extending into and out of the page. Along the slinger central channel 960, along the length of slinger 940 and extending out either end is a slinger longitudinal axis 988. Slinger 940 is mounted in slinger receptacle 892 so that slinger 940 is offset from the centers of the respective collection tubes 896, 898. Rather than the slinger spout outlet 972 being directly in line with the first tube opening center 938, there is an offset of and by an angle 992 defined by the spacing of bisecting rotor axis 984 from slinger longitudinal axis 988. Angle 992 can be varied as appropriate. The offset of slinger 940 from the respective tube opening centers accounts for angular movement of the rotor such that when in motion any fluid exiting respective first slinger spout outlets 972, 976 will land at or near respective tube opening centers 938, 932. The offset angle 992 can be varied to account for changes in the angular speed of or acceleration for the rotor 832.

When the centrifuge is run in accordance with the present teachings, fluid from the fluid collection tubes is expelled from the rotor through the tube exit channels. The expelled fluid can be accumulated, processed, or discarded using any suitable means or mechanism. For example a peripheral gutter can be employed. The peripheral gutter can include a gutter housing providing a top gutter surface, a bottom gutter surface, and gutter sidewalls extending between the top and bottom gutter surfaces along an outer gutter perimeter of the gutter housing. A gutter inlet can be located along an inner perimeter of the gutter housing. The gutter can be connected to the centrifuge housing using any means or mechanism. For example, a gutter flange extending around the gutter outer perimeter and adapted for placement on the top housing rim can be employed. The fluid collected in the peripheral gutter can be discarded using any means or mechanism. For example, a gutter outlet can be provided in the gutter housing along with a housing drainage aperture in the housing sidewall and a basin drainage aperture in the housing basin sidewall. In such a configuration, drainage tubing can be operatively associated with the gutter outlet and pass through the drainage apertures.

Figure 8:
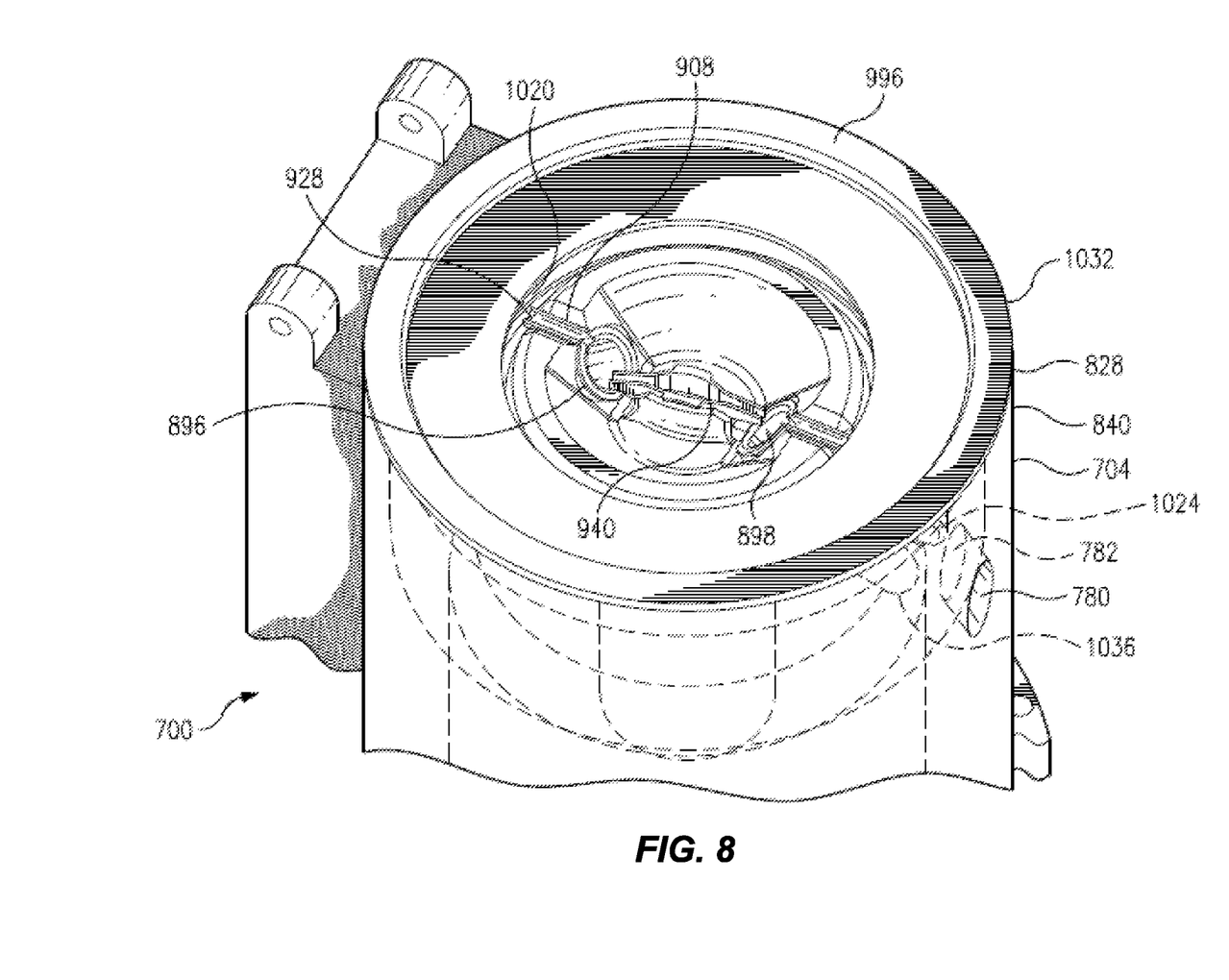
Figure 9:
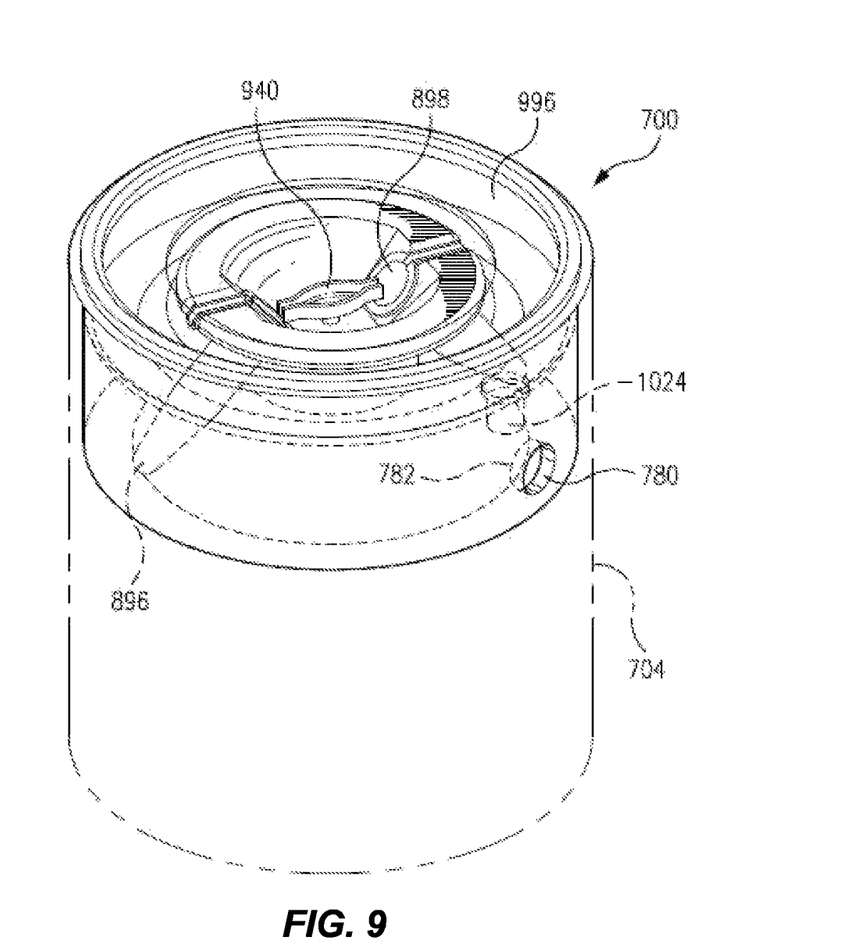

FIG. 8 shows a top perspective view of centrifuge subsystem 700 as assembled with various components including peripheral gutter 996, first and second collection tubes 896, 898, and slinger 940. A drainage tubing 1036 is shown engaged with gutter outlet 1024 and can be passed through basin drainage aperture 782 and housing drain aperture 780. A side perspective view of centrifuge subsystem 700 as assembled is also shown in FIG. 9.

Figure 10:
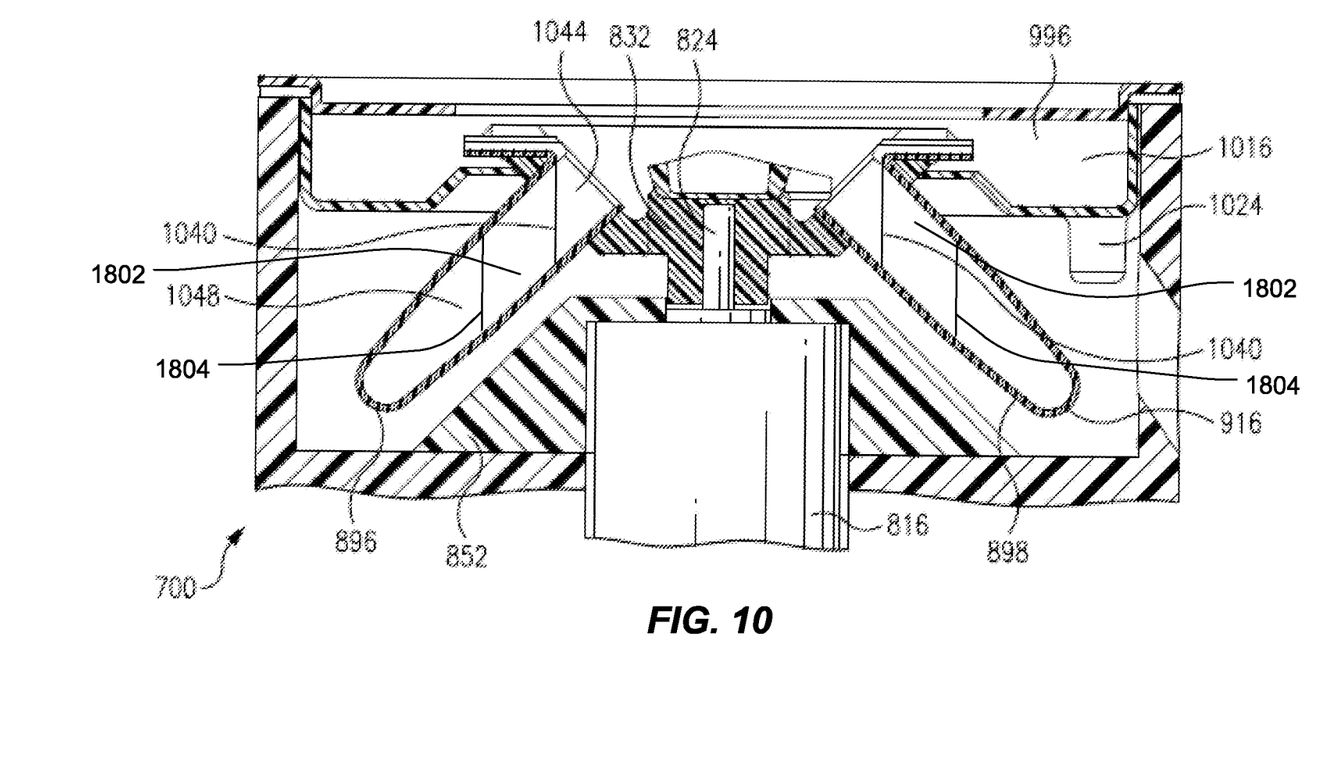

A cross-sectional view of the assembled centrifuge subsystem 700 is shown in FIG. 10. Rotor 832 rests on and is connected to rotor axle 824 of motor 816. First and second collection tubes 896, 898 are shown filled with fluid comprising an oil/air interface 1040 separating an oil phase 1044 the emulsion. Collection tubes 896,898 can comprise at least one mixing ball each in addition aqueous solution. Such bead or beads are located at the base or second tube end 916. When the rotor is in angular momentum the oil phase can exit the collection tubes through the respective exit tube channels and land in peripheral gutter 996. Oil collected in the volume 1016 of the gutter 996 can drain through port 1024.

When in the centrifuge, the surfactant solution 1048 is disposed with the volume of the centrifuge tube and resides proximal to the lower or distal end of the centrifuge tube. Once hydrophobic liquid 1802 is applied over the surfactant solution 1048, a liquids interface 1804 is formed. The hydrophobic liquid forms an upper interface 1040. When the emulsion hits the upper interface 1040, the dispersed phase of the emulsion is driven through the hydrophobic liquid 1802 to the liquids interface 1804. The aqueous phase of the emulsion enters the surfactant solution 1048. As the continuous phase of the emulsion fills the centrifuge tube, the level of hydrophobic liquid increases and excess liquid is driven out of the collection tubes and into the gutter 996.

The centrifuge of the present teachings is particular suitable for the breaking of emulsions. The emulsion can be in form a sample, i.e., source fluid. Any means or mechanism can be employed to deliver source fluid to the centrifuge. The sample fluid can be delivered through an inlet supply line (fluid supply line). When a lid is not employed, or is not in a closed configuration, the fluid line can be delivered directly into the centrifuge through the top centrifuge opening afforded by the centrifuge housing sidewalls. When a lid is employed and is in a closed configuration, the fluid supply line can pass through at least one of a lid aperture and a housing aperture to gain access to the interior of the centrifuge. For example, the lid can comprise a housing with a top lid surface and a bottom lid surface, a lid aperture extending from the top lid surface to the bottom lid surface. The lid aperture can be located anywhere on the lid, for example, it can be centrally located. More than one lid aperture can be provided. The lid aperture can be configured to accept a fluid supply line and positioned above the fluid distribution device when the lid is in a closed configuration. A fluid supply source can be in fluid communication with the fluid supply line. A fluid supply pump can be configured to pump fluid from the fluid supply source, through the fluid supply line and into the centrifuge.

Figure 11:
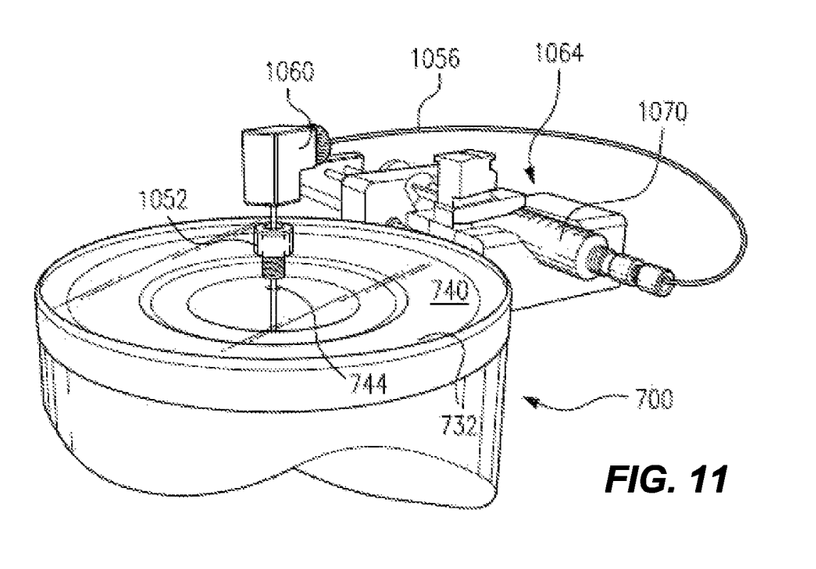

Centrifuge subsystem 700 is shown in FIG. 11 in a closed configuration and operably connected to a fluid source. A lid aperture adapter 1052 is connected to centrifuge subsystem 700 through central lid aperture 744. Inlet fluid line 1056 can pass either directly into centrifuge subsystem 700 or through one or more of a lid aperture adapter and a fluid line connector 1060. Fluid line 1056 can originate from a fluid sample source 1070. Fluid sample source 1070 can be supplied to centrifuge subsystem 700 by means of a fluid sample source pump 1064. As shown in FIG. 11, pump 1064 is a syringe style pump. The present teachings allow for use of other types of pumps as well or in addition to a syringe style pump. For example, a peristaltic pump or diaphragm pump could be employed as pump 1064. Fluid line 1056 can originate from an emulsion subsystem 300. The sample fluid supplied by inlet fluid 1056 can comprise a water-in-oil emulsion. The water phase of the water and oil emulsion can comprise microreactors that in turn can contain PCR product or products.

The above system and method of recovering a bead support from an emulsion provides particular technical advantages over other recovery processes. In particular, the above methods improve recovery of bead supports, expressed as a percent recovery.

In a first aspect, a method of recovering a bead support from an emulsion includes supplying an aqueous surfactant solution into a centrifuge tube; supplying a hydrophobic liquid over the surfactant solution in the centrifuge tube, wherein a ratio of the volume of the aqueous surfactant solution to the volume of the hydrophobic liquid is not greater than 0.5; and applying an emulsion over the hydrophobic liquid while centrifuging, the emulsion comprising a dispersed aqueous phase including the bead support, the emulsion breaking and material of the dispersed phase preferentially partitioning to the surfactant solution.

In an example of the first aspect, the ratio is not greater than 0.25. For example, the ratio is not greater than 0.1, such as not greater than 0.05. In particular, the ratio is at least 0.01.

In another example of the first aspect and the above examples, supplying the hydrophobic liquid includes supplying the hydrophobic liquid while centrifuging.

In a further example of the first aspect and the above examples, the method further includes preparing the emulsion including the dispersed phase including the bead support. For example, the method further includes amplifying a target polynucleotide to generate amplified polynucleotide on the bead support. In an example, amplifying include performing polymerase chain reaction. In another example, amplifying include performing RPA.

In an additional example of the first aspect and the above examples, the method further includes washing the separated bead support. For example, the method further includes applying the separated bead support to a sequencing device.

In another example of the first aspect and the above examples, the surfactant solution includes a surfactant in an amount in a range of 0.1% to 10%.

In a further example of the first aspect and the above examples, the surfactant solution includes a nonionic surfactant.

In an additional example of the first aspect and the above examples, the nonionic surfactant includes a polyethylene glycol ether.

In another example of the first aspect and the above examples, the surfactant solution includes an anionic surfactant. For example, the anionic surfactant includes a sulfonate surfactant. In another example, the sulfonate surfactant includes dodecyl benzene sulfonic acid or a salt thereof.

In a further example of the first aspect and the above examples, the surfactant solution includes a fluorosurfactant. For example, the fluorosurfactant is an ethoxylated nonionic fluorosurfactant.

In a second aspect, a method of recovering a bead support from an emulsion includes supplying an aqueous surfactant solution into a centrifuge tube; supplying a hydrophobic liquid over the surfactant solution in the centrifuge tube, wherein a ratio of the volume of the aqueous surfactant solution to the volume of the hydrophobic liquid is not greater than 0.5; and applying an emulsion over the hydrophobic liquid while centrifuging, the emulsion comprising a dispersed aqueous phase including the bead support, the emulsion breaking and material of the dispersed phase preferentially partitioning to the surfactant solution.

In an example of the second aspect, the ratio is not greater than 0.25, such as not greater than 0.1, or not greater than 0.05, and at least 0.01.

In another example of the second aspect and the above example, supplying the hydrophobic liquid includes supplying the hydrophobic liquid while centrifuging.

In a further example of the second aspect and the above example, the method further includes preparing the emulsion including the dispersed phase including the bead support. For example, the method further includes amplifying a target polynucleotide to generate amplified polynucleotide on the bead support. In another example, amplifying include performing polymerase chain reaction. In an additional example, amplifying include performing recombinase polymerase amplification.

In an additional example of the second aspect and the above example, the method further includes washing the separated bead support. For example, the method further includes applying the separated bead support to a sequencing device.

In another example of the second aspect and the above example, the surfactant solution includes surfactant in a total amount in a range of 0.01% to 20.0%.

In a further example of the second aspect and the above example, the surfactant solution includes a nonionic surfactant. For example, the nonionic surfactant is selected from the group consisting of a polyethylene glycol-based surfactant, an alkyl pyrrolidine surfactant, an alkyl imidazolidinone surfactant, an alkyl morpholine surfactant, an alkyl imidazole surfactant, an alkyl imidazoline surfactant, and a combination thereof. In a particular example, the nonionic surfactant includes an alkyl pyrrolidine.

In an additional example of the second aspect and the above example, the surfactant solution includes an anionic surfactant. For example, the anionic surfactant includes a sulfonate surfactant. For example, the sulfonate surfactant include dodecyl benzene sulfonic acid or a salt thereof.

In a further example of the second aspect and the above example, the surfactant solution includes an anionic surfactant in a range of 5.0% to 15.0% and includes a non-ionic surfactant in a range of 0.05% to 8.0%.

In a third aspect, a method of recovering a bead support from an emulsion includes supplying an aqueous surfactant solution into a centrifuge tube, the surfactant solution includes an anionic surfactant in a range of 5.0% to 15.0% and includes a non-ionic surfactant in a range of 0.05% to 8.0%; and applying an emulsion into the centrifuge tube while centrifuging, the emulsion comprising a dispersed aqueous phase including the bead support and a continuous phase comprising a hydrophobic liquid, the emulsion breaking and material of the dispersed phase preferentially partitioning to the surfactant solution.

In an example of the third aspect, a ratio of the volume of the aqueous surfactant solution to the volume of the centrifuge tube is not greater than 0.5. For example, the ratio is not greater than 0.25, not greater than 0.1 or not greater than 0.05 and at least 0.01.

In another example of the third aspect and the above example, the method further includes preparing the emulsion including the dispersed phase including the bead support. In an additional example, the method further includes amplifying a target polynucleotide to generate amplified polynucleotide on the bead support.

In a further example of the third aspect and the above example, the method further includes washing the separated bead support. For example, the method further includes applying the separated bead support to a sequencing device. In an example, the nonionic surfactant is selected from the group consisting of a polyethylene glycol-based surfactant, an alkyl pyrrolidine surfactant, an alkyl imidazolidinone surfactant, an alkyl morpholine surfactant, an alkyl imidazole surfactant, an alkyl imidazoline surfactant, and a combination thereof. For example, the nonionic surfactant includes an alkyl pyrrolidine.

In an additional example of the third aspect and the above example, the anionic surfactant includes a sulfonate surfactant. For example, the sulfonate surfactant include dodecyl benzene sulfonic acid or a salt thereof.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of recovering a bead support from an emulsion, the method comprising:
   supplying an aqueous surfactant solution into a centrifuge tube;
   supplying a hydrophobic liquid over the surfactant solution in the centrifuge tube, wherein a ratio of the volume of the aqueous surfactant solution to the volume of the hydrophobic liquid is not greater than 0.5 and at least 0.01; and
   applying an emulsion over the hydrophobic liquid while centrifuging, the emulsion comprising a dispersed aqueous phase including the bead support, the emulsion breaking and material of the dispersed phase preferentially partitioning to the surfactant solution.

2. The method of claim 1, wherein the ratio is not greater than 0.25.

3. The method of claim 1, wherein supplying the hydrophobic liquid includes supplying the hydrophobic liquid while centrifuging.

4. The method of claim 1, further comprising preparing the emulsion including the dispersed phase including the bead support.

5. The method of claim 1, further comprising washing the separated bead support.

6. The method of claim 5, further comprising applying the separated bead support to a sequencing device.

7. The method of claim 1, wherein the surfactant solution includes surfactant in a total amount in a range of 0.01% to 20.0%.

8. The method of claim 1, wherein the surfactant solution includes a nonionic surfactant.

9. The method of claim 8, wherein the nonionic surfactant is selected from the group consisting of a polyethylene glycol-based surfactant, an alkyl pyrrolidine surfactant, an alkyl imidazolidinone surfactant, an alkyl morpholine surfactant, an alkyl imidazole surfactant, an alkyl imidazoline surfactant, and a combination thereof.

10. The method of claim 9, wherein the nonionic surfactant includes an alkyl pyrrolidine.

11. The method of claim 1, wherein the surfactant solution includes an anionic surfactant.

12. The method of claim 11, wherein the anionic surfactant includes a sulfonate surfactant.

13. The method of claim 12, wherein the sulfonate surfactant includes dodecyl benzene sulfonic acid or a salt thereof.

14. The method of claim 1, wherein the surfactant solution includes an anionic surfactant in a range of 5.0% to 15.0% and includes a non-ionic surfactant in a range of 0.05% to 8.0%.

15. A method of recovering a bead support from an emulsion, the method comprising:
supplying an aqueous surfactant solution into a centrifuge tube, the surfactant solution includes an anionic surfactant in a range of 5.0% to 15.0% and includes a non-ionic surfactant in a range of 0.05% to 8.0%; and
applying an emulsion into the centrifuge tube while centrifuging, the emulsion comprising a dispersed aqueous phase including the bead support and a continuous phase comprising a hydrophobic liquid, the emulsion breaking and material of the dispersed phase preferentially partitioning to the surfactant solution.

16. The method of claim 15, wherein a ratio of the volume of the aqueous surfactant solution to the volume of the centrifuge tube is not greater than 0.5 and at least 0.01.

17. The method of claim 15, wherein the nonionic surfactant is selected from the group consisting of a polyethylene glycol-based surfactant, an alkyl pyrrolidine surfactant, an alkyl imidazolidinone surfactant, an alkyl morpholine surfactant, an alkyl imidazole surfactant, an alkyl imidazoline surfactant, and a combination thereof.

18. The method of claim 17, wherein the nonionic surfactant includes an alkyl pyrrolidine.

19. The method of claim 15, wherein the anionic surfactant includes a sulfonate surfactant.

20. The method of claim 19, wherein the sulfonate surfactant include dodecyl benzene sulfonic acid or a salt thereof.

* * * * *